United States Patent
Ling

(10) Patent No.: US 10,537,605 B2
(45) Date of Patent: Jan. 21, 2020

(54) COMPOSITION OF PLANT EXTRACT AND ITS PHARMACEUTICAL COMPOSITION AND APPLICATION THEREOF

(71) Applicant: CALIWAY BIOPHARMACEUTICALS CO., LTD., New Taipei (TW)

(72) Inventor: Yu-Fang Ling, Taipei (TW)

(73) Assignee: CALIWAY BIOPHARMACEUTICALS CO., LTD., New Taipei (TW)

( * ) Notice: Subject to any disclaimer, the term of this patent is extended or adjusted under 35 U.S.C. 154(b) by 0 days.

(21) Appl. No.: 15/025,898

(22) PCT Filed: Aug. 28, 2015

(86) PCT No.: PCT/CN2015/088338
§ 371 (c)(1),
(2) Date: Mar. 30, 2016

(87) PCT Pub. No.: WO2016/029868
PCT Pub. Date: Mar. 3, 2016

(65) Prior Publication Data
US 2017/0157194 A1   Jun. 8, 2017

Related U.S. Application Data

(60) Provisional application No. 62/042,955, filed on Aug. 28, 2014.

(51) Int. Cl.
*A61K 36/9066* (2006.01)
*A61K 36/82* (2006.01)

(52) U.S. Cl.
CPC .......... *A61K 36/9066* (2013.01); *A61K 36/82* (2013.01); *A61K 2121/00* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,475,530 B1 | 11/2002 | Kuhrts | |
| 2003/0185912 A1 | 10/2003 | Rosenbloom | |
| 2005/0147697 A1 | 7/2005 | Rosenbloom | |
| 2006/0172012 A1 | 8/2006 | Finley et al. | |
| 2008/0233218 A1 | 9/2008 | Newmark et al. | |
| 2009/0239943 A1 | 9/2009 | Sarkar | |
| 2012/0177623 A1 | 7/2012 | Naghavi et al. | |
| 2014/0141082 A1 | 5/2014 | Gao | |

FOREIGN PATENT DOCUMENTS

| | | | |
|---|---|---|---|
| CN | 101095665 A | | 1/2008 |
| CN | 101632655 A | | 1/2010 |
| CN | 101695324 A | * | 4/2010 |
| CN | 101695324 A | | 4/2010 |
| CN | 102357226 A | | 2/2012 |
| CN | 103479972 | | 1/2014 |
| JP | 2012044982 A | * | 3/2012 |
| WO | WO2007041276 A2 | | 4/2007 |
| WO | WO2008120220 A1 | | 10/2008 |
| WO | WO2010048114 A1 | | 4/2010 |
| WO | WO2013016257 A1 | | 1/2013 |
| WO | WO2014028607 | | 2/2014 |
| WO | WO2014111811 A1 | | 7/2014 |

OTHER PUBLICATIONS

Translation of JP 2012-044982 A. Kitamura H. Mar. 8, 2012 (Year: 2012).*
Meydani et al, "Dietary polyphenols and obesity", Nutrients, Jul. 2010; 2: 737-751.
Most et al, "Short-term supplementation with a specific combination of dietary polyphenols increases energy expenditure and alters substrate metabolism in overweight subjects", Int J Obesity, May 2014; 38(5):698-706.
Shu Wang et al., "Novel insights of dietary polyphenols and obesity", J Nutr Biochem. Jan. 2014, pp. 1-39, 2013 Elsevier Inc.
Thérèse Sergent et al., "Phenolic compounds and plant extracts as potential natural anti-obesity substances", Available online Apr. 21, 2012, pp. 68-73, Food Chemistry, Elsevier Ltd.
Dong-Hu Zhou et al., "Combination of Low Concentration of (—)-Epigallocatechin Gallate (EGCG) and Curcumin Strongly Suppresses the Growth of Non-Small Cell Lung Cancer in Vitro and in Vivo through Causing Cell Cycle Arrest", Published: Jun. 5, 2013, pp. 12023-12036, Int. J. Mol. Sci.
Mustika Ratu, "Slimming tea", Aug. 2009, http://www.gnpd.com.
New Chapter, "Whole Body Health Inflammation Response Dietary Supplement", Jun. 2014, http://www.gnpd.com.

* cited by examiner

*Primary Examiner* — Amy L Clark
(74) *Attorney, Agent, or Firm* — WPAT, PC

(57) ABSTRACT

Provided is a plant extract composition and a pharmaceutical composition thereof for reducing body weight and body fat, wherein the plant extract composition comprises a green tea extract and a turmeric extract respectively 30 wt % to 75 wt % and 20 wt % to 55 wt % of a total weight of the composition. In diet-induced obesity models, either obesity is induced first or simultaneously with administration, the plant extract composition and a pharmaceutical composition thereof can reduce body weight and body fat more significantly than a single plant extract or commercially available weight loss drugs.

13 Claims, 4 Drawing Sheets

COMPOSITION OF PLANT EXTRACT AND ITS PHARMACEUTICAL COMPOSITION AND APPLICATION THEREOF

BACKGROUND OF THE INVENTION

1. Field of the Invention

The present invention relates to a composition obtained from plant extracts, and more particularly to the composition comprising a specific ratio of green tea extract to turmeric extract. The present invention also relates to an application of the composition, and more particularly for promoting weight loss and reducing body fat. The present invention also relates to a pharmaceutical composition, and more particularly to the pharmaceutical composition comprising the above-said composition. The present invention also relates to an application of the pharmaceutical composition, and more particularly for promoting weight loss and reducing body fat.

2. Description of the Prior Arts

As defined by the World Health Organization (WHO), the body mass index (BMI) greater than 25 is classified as overweight and BMI greater than 30 as obesity. According to the global statistics in 2014, the population of overweight and obesity is over 2.7 billion, of which approximately 13% population would be obese. These obese people suffer from cardiovascular diseases, hyperlipidemia, diabetes, and cancers at sharply higher probabilities than the average. According to the report of the WHO, among the global leading risks for mortality caused by diseases, overweight and obesity ranked 6th, and at least more than 3.4 million adults die of chronic diseases caused by overweight or obesity in 2013, wherein the medical burden of 44% of diabetes and 23% of ischemic heart disease are attributable to obesity. Studies also showed that the age of obese people is in a gradually downward trend. Approximately 40 million children under age five are overweight worldwide in 2011. According to the report by the Johns Hopkins University Bloomberg School of Public Health published in 2007, approximately 75% and 41% adults would be overweight and obese, respectively, in the USA in 2015. With the rising of developing countries, the population of obesity is rapidly increasing and obesity becomes one of the major epidemics. The Centers for Disease Control and Prevention (CDC) in the USA noted that the population of obese adults in the USA is more than 72 million, and 40% of global obese population is in Asia. The population of overweight and obese adults was increased from 25% to 38.5% in China from 2002 to 2010. Moreover, in 2015, the overweight population will be 50% to 57% in China.

Obesity is a health problem around the world, and the causes of obesity are complex with multiple factors involved. More and more evidences show that obesity is not only a simple self-control problem, but also involves appetite regulation and energy metabolism. Obesity not only increases mortality and causes huge medical burden to mankind, but also affects life quality. Though the cause of obesity is not completely established, it is believed to be related to genetics, metabolism, biochemistry, culture and psychological factors. Accordingly, many causes of death are considered to be correlated with obesity including cancers, cardiovascular diseases, diabetes, chronic lower respiratory diseases, chronic hepatic disease and liver cirrhosis, hypertensive diseases, renal disease, etc., all of which make obesity a global issue. Recently, the prevalence of obesity is rising accompanied by the metabolic abnormality in blood pressure, blood sugar, insulin resistance, and dyslipidemia, which gradually leads to the incidence of diabetes, cardiovascular diseases, atherosclerosis, cerebrovascular disease, stroke, myocardial infarction, and eventually death.

The mechanisms of current drugs for losing weight can be divided into two categories, one is appetite suppression, and the other is blocking the intestinal absorption of dietary fat; wherein the main mechanism of marketed weight loss drugs is appetite suppression, the drugs comprising Sibutramine (Reductil®), Lorcaserin (Belviq®), Qsymia®, Contrave, etc, which have severe side effects and high risk of cardiovascular diseases. Take off-shelve weight loss drug Sibutramine (Reductil®) for example, once having a market share as high as 70 percent, Sibutramine (Reductil®) is to dually increase the satiety effect through the central nervous system and the metabolic rate in the periphery to achieve the weight loss effect. Sibutramine (Reductil®) is a noradrenaline and serotonin reuptake inhibitor which increases satiety to suppress appetite and therefore achieves the purpose of weight loss, wherein satiety increase is through the inhibiting of serotonin and noradrenaline reuptake via α1-adrenoceptors, β1-adrenoceptors and 5-HT2 receptor subtypes. Sibutramine (Reductil®) may cause high blood pressure and increase heart rate and was proved to increase cardiovascular risks in recent years, therefore, the drugs containing Sibutramine (Reductil®) ingredients were recalled from the markets of Europe, the United States, Australia, Taiwan and other countries in 2010.

Orlistat (Xenical®) blocks the intestinal dietary fat absorption and is the only legitimate weight loss drug for long-term use in most countries. It is a specific, reversible gastrointestinal lipolysis enzyme inhibitor in the stomach and small intestine. Orlistat (Xenical®) and lipase secreted from stomach and pancreas will form a covalent bond in the serine of the activation site of lipase to inactivate lipase activity as to inhibit the hydrolysis of triglyceride in dietary fat to absorbable free fatty acids and monoglycerides. Undigested triglycerides are unabsorbable and will be excreted directly. By means of inhibiting digestion enzymes secreted from pancreatic and intestine, the intestinal absorption of fat could be reduced up to 25% to 30%. Moreover, as the mechanism of Orlistat (Xenical®) is blocking fat absorption, some significant side effects were found including oil stool, increasing bowel movement, bloating related to gastrointestinal tract, interfering fat-soluble vitamin absorption, liver damage, gallstones, etc.

Massive demand and high profits of weight loss drugs have drawn pharmaceutical companies to researches and investment thereon. However, the safety of weight loss drugs is a challenging issue, especially severe side effects and the risk of cardiovascular disease. Therefore, the FDA had stopped approving weight loss drugs for years before 2012, causing inactivity of the pharmaceutical market. In 2012, FDA finally approved another four weight loss drugs, respectively Lorcaserin (Belviq®), Qsymia®, Contrave and Saxenda®, expected to bloom the market of weight loss drugs again.

The main ingredients of Qsymia® and Lorcaserin (Belviq®) are respectively phentermine-topiramate and lorcaserin, the main mechanism of them is increasing satiety and suppressing appetite to achieve weight loss purposes. Phentermine and topiramate are both old components of drug ingredients, wherein phentermine is a central sympathomimetics, and the mechanism of phentermine is suppressing appetite by stimulating adrenal gland to secret norepinephrine through hypothalamus; wherein the mechanism of topiramate is to promote the activity of the neurotransmitter GABA, blocking sodium channels, antagonizing glutamine receptor and inhibiting carbonic anhydrase to inhibit appetite and increase satiety. However, as early as in 1997, 24 cases of valvular heart disease were reported after taking weight loss drugs containing phentermine Fen-Phen (fenfluramine/dexfenfluramine-phentermine) drove FDA to recall fenfluramine and dexfenfluramine from the market. Phentermine is contraindicated for patients at high cardiovascular risk in many countries. Topiramate has been approved to treat epilepsy. The side effects of Phentermine-topiramate drug include tingling hands and feet, dizziness, dysgeusia, insomnia, constipation, and dry mouth. Lorcaserin (Belviq®) is a 5-HT2C receptor activator, by activating hypothalamic pro-opiomelanocortin neurons (POMC neurons) to produce melanocyte stimulating hormone ($\alpha$-MSH), and followed by inducing satiety, suppressing appetite and reducing dietary energy intake. Lorcaserin (Belviq®) is highly specific to 5-HT2C receptors instead of 5-HT2A and 5-HT2B receptors hence reduced the risk of severe cardiovascular diseases. As the side effects of Lorcaserin (Belviq®) include valve damage, headache, nausea, fatigue and urinary tract infections, FDA still requires the industry to conduct follow-up clinical monitoring, medication should be ceased if no significant weight loss after three months of Lorcaserin (Belviq®) treatment.

Contrave® is a dopamine and norepinephrine reuptake inhibitor, acting on the central nervous system to suppress appetite. The side effects of Contrave® are suicidal tendency, nausea, constipation, headache, vomiting, and dizziness. Saxenda® is a weight-loss drug administered by subcutaneous injection, and the main mechanism of Saxenda is mainly by reducing the rate of gastric emptying and increasing satiety to achieve the purpose of weight loss; the side effects are nausea, hypoglycemia, diarrhea, constipation, vomiting, headache, loss of appetite and etc. Overall, the risk of cardiovascular disease and the safety of long-term use of new weight loss drugs remained to be monitored for longer period. Because of numerous side effects and safety concerns, these new weight loss drugs are not suitable for patients with cardiovascular diseases, especially Qsymia® which contains phentermine and reported to cause severe cardiovascular diseases made Qsymia® still forbidden in Taiwan and many other countries.

The main concern of weight loss drugs is the cardiovascular risk or mental safety such as dizziness, insomnia, palpitations, constipation and other side effects for long-term use. As the currently approved weight loss drugs have severe side effects, poor tolerance, and cardiovascular risk, the pharmaceutical market of weight loss drugs has not grown in pace with the global obese population and demand. Five among ten approved anti-obesity drugs from 1957 to 2014 which act through the mechanism involving appetite inhibition were recalled by FDA for their CVD risks or psychiatric safety concern included Sibutramine (trade name Reductil®) which launched in 2002 and shared 70% market revenue.

To overcome the described side effects and safety concern found in the launched weight loss products, better drugs developed based on weight loss function and reduction of CVD risk factors are urgently required.

SUMMARY OF THE INVENTION

To overcome the shortcomings of side effects and cardiovascular risks of currently weight loss drugs. The objective of the present invention is to provide a plant extract composition for promoting weight loss and reducing body fat. The composition comprises a green tea extract and a turmeric extract, and the percentages of green tea extract and turmeric extract are respectively 30 wt % to 75 wt % and 20 wt % to 55 wt % of a total weight of the composition. Preferably, the plant extract composition further comprises resveratrol, wherein a percentage of the resveratrol is between 0 wt % and 30 wt % of the total weight of the composition. It is notable that treatment of resveratrol or turmeric extract alone in animal experiments has no significant effects on reducing body weight and body fat which was consistent with the previous findings. More importantly, the plant extract composition of the present invention administered simultaneously with high fat diet significantly reduced body weight and body fat in animal model. Furthermore, the plant extract composition of the present invention also significantly reduced body weight and body fat in diet-induced obese mice model. Compared to that of the commercially available weight loss drug Orlistat (Xenical®), the reduction effect of body weight and body fat of the plant extract composition of the present invention is significantly better ($p<0.001$). The better effect of the present invention was proved in the diet-induced obesity model which is more difficult than the model simultaneous administered with compositions and obesity induction to reduce body weight and body fat and is much closer to the clinical treating of overweight and obesity patients. Under the circumstances of animal model with obesity, the effects of the present invention on reduction of body weight and body fat are better than those of commercial drug or single plant extract explained the nonobviousness and novelty of the composition of the present invention.

According to the present invention, the term "turmeric extract" as used herein mainly comprises curcumins. Preferably, the amount of the curcumins in the turmeric extract is from 80% to 100%. The term "green tea extract" as used herein mainly comprises catechins, and the amount of the catechins of the total amount of the green tea extract is from 75% to 100%.

In one preferred embodiment, the present invention further provides a method for preparing the plant extract composition containing a green tea extract and a turmeric extract comprising the following steps: mixing the plant extract composition containing a green tea extract and a turmeric extract with a pharmaceutically acceptable salt, a pharmaceutically acceptable stabilizer or a pharmaceutically acceptable excipient to form capsules, tablets, film-coated tablets or injection fluids.

Preferably, the method further comprises resveratrol to form a composition containing a green tea extract, a turmeric extract and resveratrol.

Preferably, the stabilizers include, but are not limited to, xylitol, sorbitol, polydextrose, isomalt, and dextrose.

The present invention also provides a pharmaceutical composition for reducing body weight and body fat, containing the plant extract composition and the pharmaceutically acceptable excipient.

Preferably, the pharmaceutical composition further comprises an effective amount of resveratrol for reducing body weight and body fat.

According to the present invention, the term "a pharmaceutically acceptable excipient" as used herein includes, but is not limited to, disintegrant, binder, filler, lubricant, suspending agent, solubilizer, and glidant. The amount of excipient employed will depend upon quantity of the active ingredient. One excipient can perform more than one function.

Preferably, examples of disintegrant include, but are not limited to, agar, alginic acid, calcium carbonate, carboxymethylcellulose, cellulose, clays, colloidal silica, croscarmellose sodium, cross-linked povidone, gum, magnesium aluminum silicate, methyl cellulose, polacrilin potassium, sodium alginate, low substituted hydroxypropyl cellulose, crosslinked polyvinylpyrrolidone hydroxypropylcellulose, sodium starch glycolate, or starch.

Preferably, examples of binder include, but are not limited to, microcrystalline cellulose, hydroxymethyl cellulose, hydroxypropyl cellulose, or polyvinyl pyrrolidone.

Preferably, examples of filler include, but are not limited to, calcium carbonate, calcium phosphate, dibasic calcium phosphate, tribasic calcium sulfate, calcium carboxymethylcellulose, cellulose, dextrin, salt, dextrin, dextrose, fructose, lactitol, lactose, carbonate, magnesium oxide, maltitol, maltodextrin, maltose, sorbitol, starch, sucrose, sugar, or xylitol.

Preferably, examples of lubricant include, but are not limited to, agar, calcium stearate, ethyl oleate, ethyl laureate, glycerin, glyceryl palmitostearate, hydrogenated vegetable oil, magnesium oxide, magnesium stearate, mannitol, poloxamer, ethylene glycol, sodium benzoate, sodium lauryl sulfate, sodium stearoyl acid, sorbitol, stearic acid, talc or zinc stearate.

Preferably, examples of suspending agent include, but are not limited to, mannitol, carboxymethyl cellulose (CMC), or CMC-Na.

Preferably, examples of solubilizer include, but are not limited to, hydroxypropyl-beta-cyclodextrin, tween 80, castor oil or polyethylene glycol (PEG).

Preferably, examples of glidant include, but are not limited to, magnesium stearate, silicon dioxide, magnesium trisilicate, powdered cellulose, starch, talc, tribasic calcium phosphate, calcium silicate, magnesium silicate, colloidal silica or silicon hydrogel.

In accordance with the present invention, the pharmaceutical composition for reducing body weight and body fat is prepared for multiple forms, including, but not limited to, liquid, semi-solid and solid dosage, such as liquid solution (including injectable and infusible solution), dispersions, suspensions, tablets, pillars, powders, liposomes or suppositories. Preferred form depends on the mode of administration and therapeutic application of expectations. Preferably, the pharmaceutical composition of the present invention is administered orally or in the form of infusion solutions. In an embodiment of the present invention, the pharmaceutical composition at the effective amount is orally administered. According to the present invention, the formulation is preferred for pill, granules, film-coated tablets, capsules, tablets and other solid formulations are also contemplated within the scope of the present invention.

The present invention further provides a method for reducing body weight and body fat comprising a step of administering to a subject in need thereof a therapeutically effective amount of the pharmaceutical composition comprising a green tea extract and a turmeric extract; wherein the subject is an animal or a human.

Preferably, the formulation of the pharmaceutical composition is orally administered or administered by injection.

Preferably, the therapeutically effective amount of the pharmaceutical composition for a human is from 1.8 mg/kg body weight (B.W.) to 145 mg/kg B.W. More preferably, the therapeutically effective amount of the pharmaceutical composition for a human is from 5.4 mg/kg B.W. to 70 mg/kg B.W.

According to the present invention, the term "effective dose" could be calculated according to different subjects from the announcement of Table 1 of "estimating the maximum safe starting dose in initial clinical trials for therapeutics in adult healthy volunteers" from the Food and Drug Administration (FDA).

According to the present invention, the term "reducing body weight and body fat" as used herein refers to the body weight and body fat both less than the control group after administration of an effective amount of the composition comprising a green tea extract and a turmeric extract. As shown in the embodiment of the present invention, reducing body fat can be determined by administering the composition comprising a green tea extract and a turmeric extract or further comprising resveratrol in a specific dosage, and measuring the difference of epididymis fat, perinephric fat, mesenteric fat, groin fat and fat outside of peritoneal cavity in a specific period.

The components of the plant extract composition of the present invention are all extracted from plants, and the results in accordance with the present invention show that the composition of the present invention neither affects appetite or food intake, nor affects serum biochemical indicators. Therefore, the composition of the present invention is safer and less side effects compared to those of commercially available weight loss drugs. Furthermore, compared to conventional weight loss drugs, the plant extract composition not only reduces body weight, but also inhibits adipocytes growth, increases the metabolism of body fat and energy expenditure. In other words, the plant extract composition of the present invention can improve obesity fundamentally, so as to reduce the regain of body weight, improve the cardiovascular indicator including blood lipids and blood sugar as to reduce cardiovascular risks.

Therefore, the plant extract composition of the present invention provides a safer solution for modern global obesity and overweight issues, and can effectively reduce body weight and body fat for application of pharmaceutical composition or health food.

DETAILED DESCRIPTION OF THE PREFERRED EMBODIMENTS

Other objectives, advantages and novel features of the invention will become more apparent from the following detailed description when taken in conjunction with the accompanying drawings.

EXAMPLE 1

Preadipocytes Inhibition Assay

3T3-L1 preadipocytes (purchased from FIRDI, Taiwan) were seeded at a density of $1 \times 10^4$ cells/well in 96-well plates. Three repeated cell experiments were examined using 1% DMSO as control group, and 50 ppm resveratrol, 50 ppm turmeric extract, 80 ppm green tea extract and 100 ppm of the formulations ME008A, ME008D, ME001, ME00C1, and ME00D1 respectively for nine groups. After incubation for 48 hours, the inhibitory effect on 3T3-L1 preadipocytes was analyzed by MTT assay. The formulation ME008A in accordance with the present invention has 50 wt % green tea extract, 25 wt % green coffee bean extract, and 25 wt % resveratrol. The formulation ME008D in accordance with the present invention has 40 wt % green tea extract, 45 wt % green coffee bean extract, and 15 wt % resveratrol. The formulation ME001 in accordance with the present invention has 60 wt % green tea extract, 10 wt % turmeric extract, and 30 wt % resveratrol. The formulation ME00C1 in accordance with the present invention has 40 wt % green tea extract, 50 wt % turmeric extract, and 10 wt % resveratrol. The formulation ME00D1 in accordance with the present invention has 75 wt % green tea extract and 25 wt % turmeric extract. All data are presented as Mean±SD. The letters a, b, c, d, e, f, and g represent the results of the statistics, and the different letters represent statistical difference among the groups ($p<0.05$).

Figure 1:
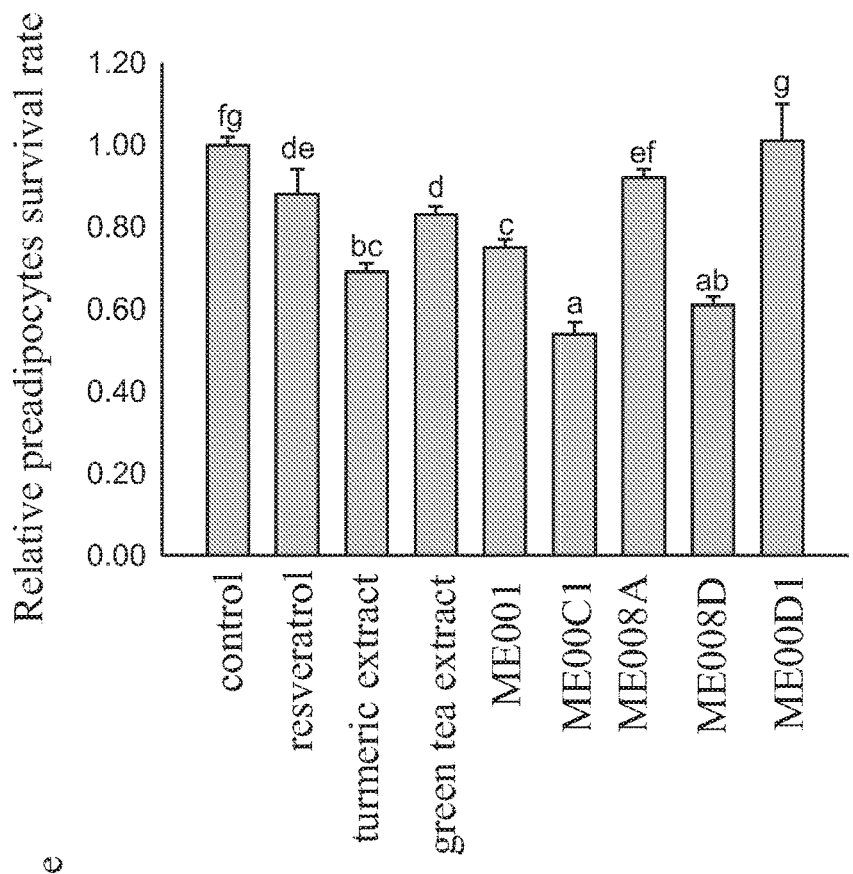
FIG. 1 illustrates the bar chart in each group for inhibiting preadipocytes growth through MTT assay.

As shown in FIG. 1, compared to the control group, the formulations ME00C1, ME001, and ME008D of the present invention all could inhibit preadipocytes growth ($p<0.05$); wherein the formulation ME00C1 had the best inhibitory effect on preadipocytes ($p<0.05$). The inhibitory effect of the formulation ME00C1 was greater than that of the resveratrol, the turmeric extract, or the green tea extract ($p<0.05$).

EXAMPLE 2

Differentiating Adipocytes Inhibition Assay

3T3-L1 cells were seeded at a density of $1 \times 10^5$ cells/well in 12-well plates for 24 hours. After seeding for further one day, medium was changed and replaced with 5 μg/ml insulin (differentiation agent), 1 μM dexamethasone, 0.5 μM 3-isobutyl-1-methylxanthine. Three repeated cell experiments were examined using 1% DMSO as control group, and 50 ppm resveratrol extract, 50 ppm turmeric extract, 80 ppm green tea extract, 100 ppm formulations ME008A, ME008D, ME001, ME00C1, and ME00D1 respectively for nine groups. After incubation for another 48 hours, the inhibitory effect on differentiating adipocytes 3T3-L1 was analyzed by MTT assay. All data are presented as Mean±SD. The letters a, b, c, d, e, and f represent the results of the statistics, and the different letters represent statistical difference among the groups ($p<0.05$).

Figure 2:
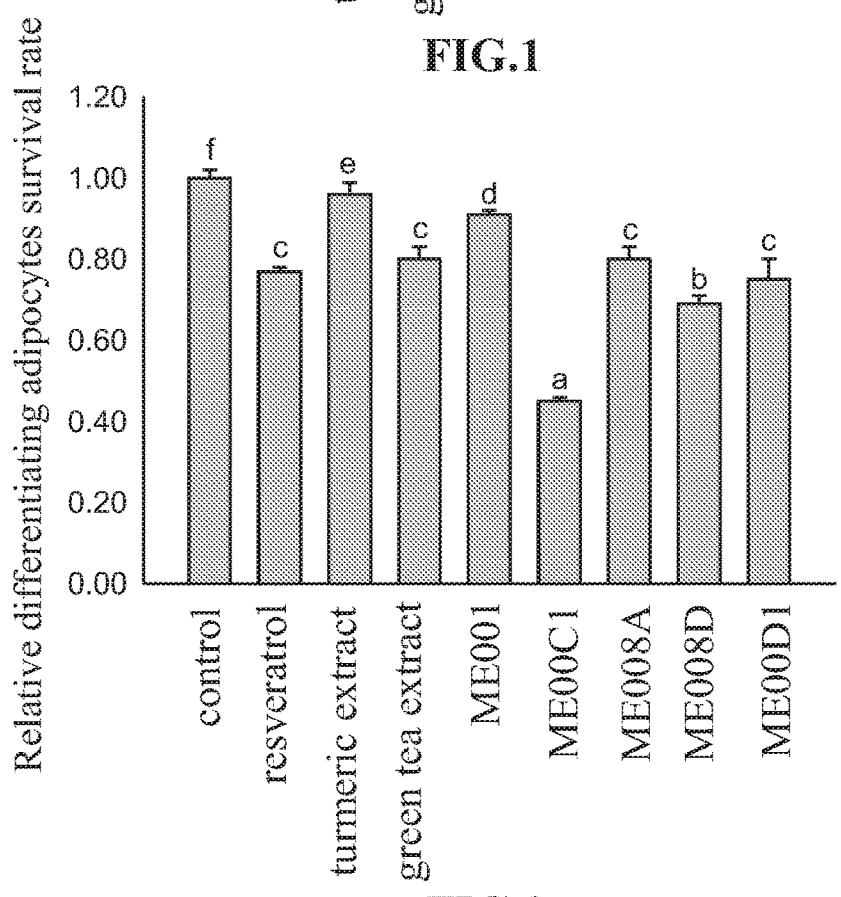
FIG. 2 illustrates the bar chart in each group for inhibiting differentiating adipocytes growth through MTT assay.

As shown in FIG. 2, compared to the control group, the formulations of the present invention all could inhibit differentiating adipocytes growth significantly, wherein formulation ME00C1 had the best inhibitory effect on differentiating adipocytes. The inhibitory effect of the formulation ME00C1 was greater than that of the resveratrol, the turmeric extract, or the green tea extract ($p<0.05$).

EXAMPLE 3

Animal Assay (I) (Obesity Induction and Administration Simultaneously)

C57/BL6 female mice aged 8 weeks were used in this example. There were five groups for test, respectively as a control group, an obese group, a resveratrol group (formulation: 61.5 mg/kg B.W.), a green tea extract group (formulation: 123 mg/kg B.W.), and an experimental group (the formulation of ME001 of the present invention: 676.5 mg/kg B.W.). Five female mice were used in each group. In duration, high fat diets were fed for all groups to induce obesity except for the control group, and resveratrol, green tea extract and the formulation of ME001 were administered respectively and simultaneously for 8 weeks, the obese group was tube-fed with sterile water to evaluate the difference of bodyweight gain and body fat of each group; meanwhile, body weight and average food intake were recorded weekly. The mice were sacrificed, the fat around the ovary, perinephric fat, and mesenteric fat were weighed and calculated to obtain visceral fat mass, and the fat around the groin and peritoneal cavity was calculated to obtain subcutaneous fat mass. All data are presented as Mean±SD. The letters a, b, c, d, e, and f represent the results of the statistics, the different letters represent statistical difference among the groups ($p<0.05$), and the identical letter represents no statistical difference among the groups ($p>0.05$).

Figure 3A:
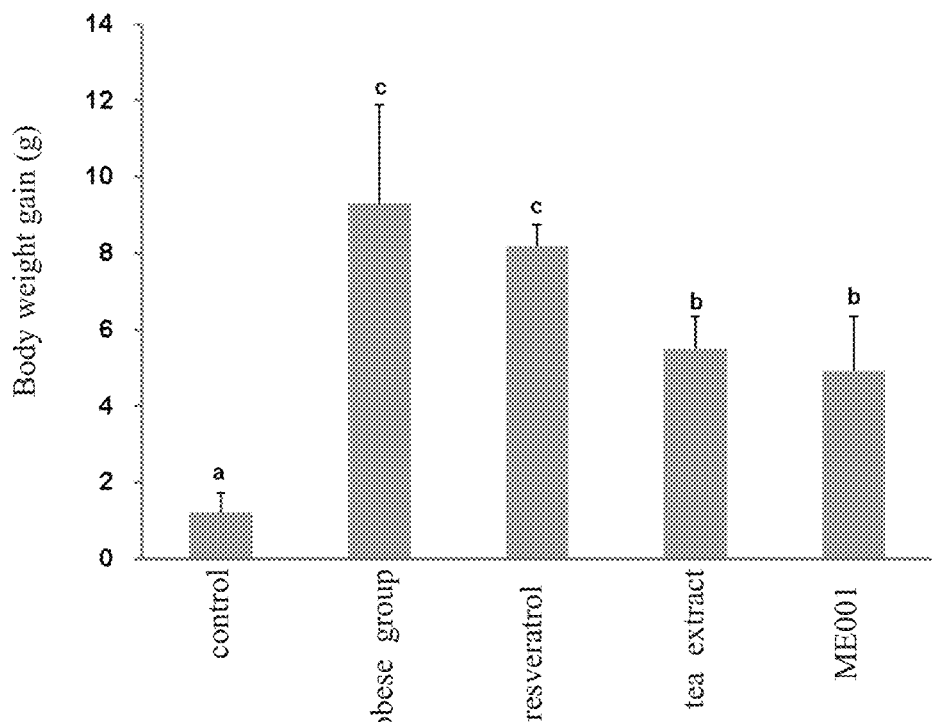
FIG. 3A illustrates the bar chart of body weight gain of mice administered with obesity induction and indicated composition simultaneously.
Figure 3B:
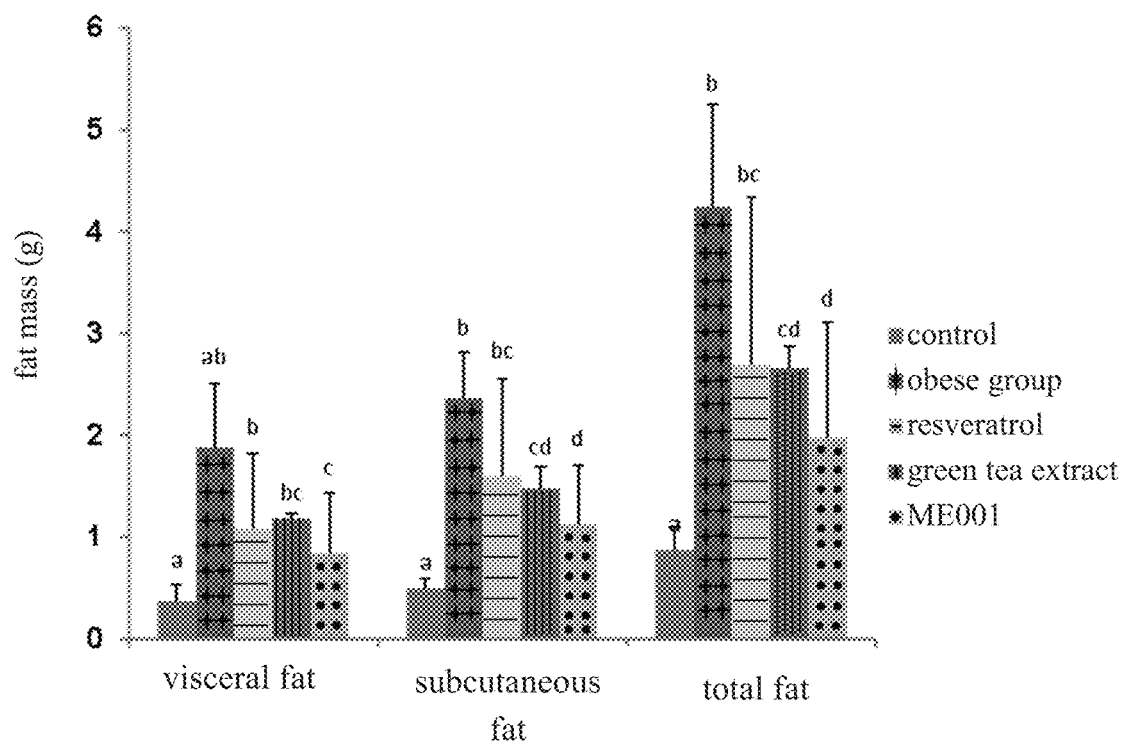
FIG. 3B illustrates the bar chart of fat mass of visceral fat, subcutaneous fat, and total fat mass of mice administered with obesity induction and indicated composition simultaneously.

As shown in FIGS. 3A and 3B, the body weight gain of the formulation ME001 was significantly lower than that of obese group by 47.2% ($p<0.05$). Therefore, the formulation ME001 of the present invention can reduce the body weight effectively ($p<0.05$). In contrast, the body weight gain, the amount of visceral fat, subcutaneous fat, and body fat of the resveratrol group showed no statistical difference compared to the obese group ($p>0.05$).

Compared to the obese group, the formulation ME001 of the present invention could reduce the amount of visceral fat, subcutaneous fat, and body fat significantly ($p<0.05$). Besides, compared to those of other groups, the formulation ME001 of the present invention can also reduce body weight and body fat, and the effect was better than those of single plant extract groups such as the resveratrol group and the green tea extract group ($p<0.05$). In experimental periods, no statistical difference was found in the daily food intake in mice fed with a high-fat diet ($p>0.05$).

EXAMPLE 4

Animal Assay (II) (Obesity Induction First and Then Administration)

C57/BL6 female mice aged 8 weeks were used in this example. All groups were fed with high fat diets except the control group for six weeks to obtain diet-induced obese mice (the weight gain was over 20%). The obese mice were divided into seven groups for test, respectively as an obese group, an Orlistat (Xenical®) group (formulation: 34.8 mg/kg B.W.), a turmeric extract group (formulation: 41 mg/kg B.W.), and four experimental groups such as the formulation ME008A (formulation: 676.5 mg/kg B.W.), the formulation ME008D (formulation: 676.5 mg/kg B.W.), the formulation ME001 (formulation: 676.5 mg/kg B.W.), and the formulation ME00C1 (formulation: 651.9 mg/kg B.W.). Five female mice were used in each group. High fat diets were fed for all groups to induce obesity except for the control group, and Orlistat (Xenical®), turmeric extract and the formulations of ME008A, ME008D, ME001, and ME00C1 were administered respectively, the obese group was tube-fed with equal volume sterile water for eight weeks, to evaluate the difference of body weight gain and body fat of each group; meanwhile, the body weight and the average food intake were recorded weekly. The mice were sacrificed, the fat around the ovary, perinephric fat, and mesenteric fat were weighed and calculated to obtain visceral fat mass, and the fat around the groin and peritoneal cavity was calculated to obtain subcutaneous fat mass. All data are presented as Mean SD. The letters a, b, c, d, and e represent the results of the statistics, the different letters represent statistical difference among the groups (p<0.05), and the identical letter represents no statistical difference among the groups (p>0.05).

Figure 4A:
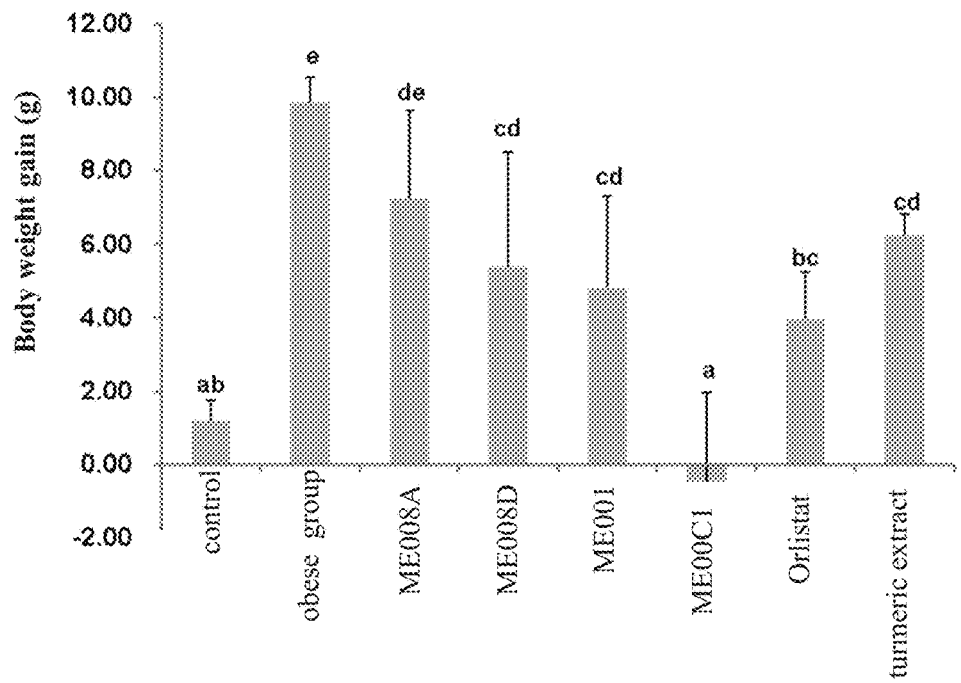
FIG. 4A illustrates the bar chart of body weight gain of diet-induced obese mice administered with indicated compositions.
Figure 4B:
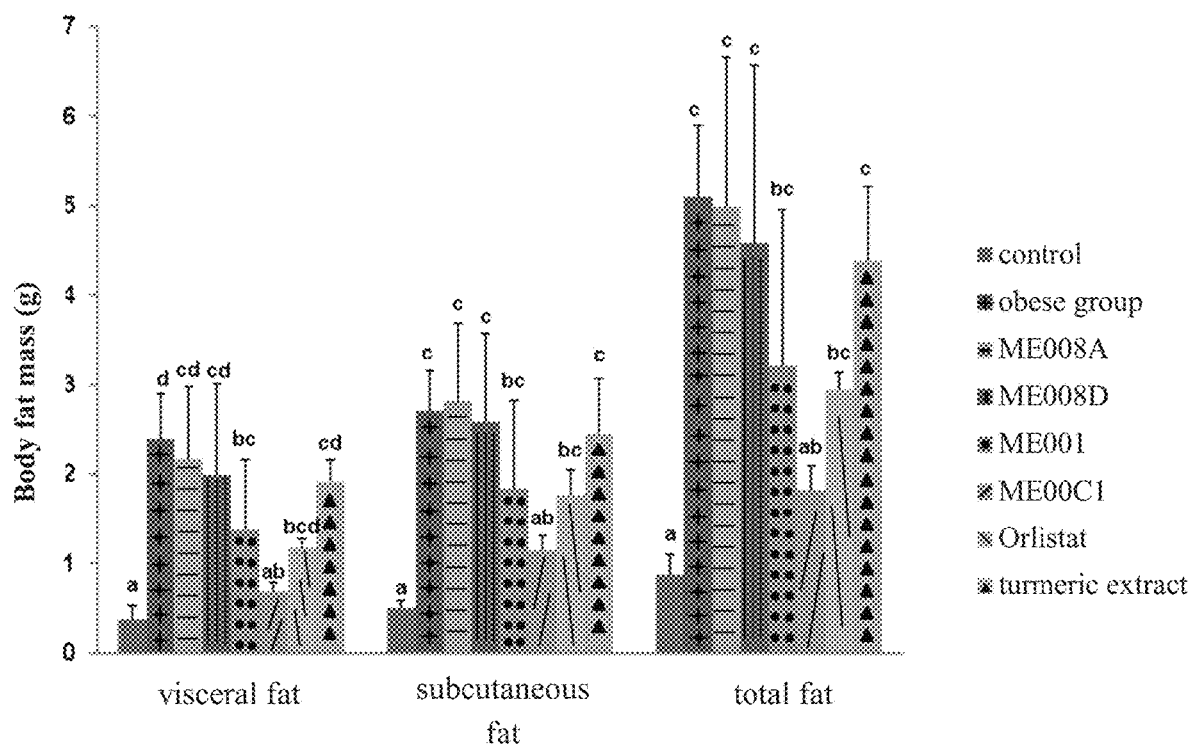
FIG. 4B illustrates the bar chart of fat mass of visceral fat, subcutaneous fat, and total fat mass of diet-induced obese mice administered with indicated compositions.

As shown in FIGS. 4A and 4B, the body weight gain of the obese group was significantly higher than that of the control group by 87.7% (p <0.05) representing that obesity was induced successfully. The formulations of ME008D, ME001, and ME00C1 of the present invention can reduce the gain of body weight significantly (p <0.05), wherein the formulation ME00C1 had the best reduction effect on the gain of body weight, specifically, better than that of the Orlistat (Xenical®) group (p <0.05) and the turmeric extract group (p <0.05).

The body fat mass(comprising visceral fat and subcutaneous fat) of the groups of formulations ME008D, ME001, and ME00C1 of the present invention were reduced significantly (p <0.05), wherein the body fat was decreased by 10.3%, 36.9%, and 64.1% respectively. The formulation ME00C1 had the best reduction effect on the gain of body fat, better than those of the Orlistat (Xenical®) group (p <0.05) and the turmeric extract group (p <0.05). Therefore, the formulation ME00C1 of the present invention can reduce body weight and body fat more effectively than other groups. In experimental duration, mice in each group fed with a high-fat diet showed no statistical difference (p>0.05).

EXAMPLE 5

Animal Assay (III) (Obesity Induction and Administration Simultaneously)

Sprague-Dawley (SD) male rats aged 8 weeks were used in this example. There were four groups for test, respectively as a control group, an obese group, two experimental groups with formulation ME00C1 (formulation: 199.6 mg/kg BW) and formulation ME00C1A (formulation: 186 mg/kg BW), wherein the formulation ME00C1A in accordance with the present invention has 55.5 wt % green tea extract and 44.5 wt % turmeric extract. Six rats were used in each group. High fat diets were fed for all groups to induce obesity except for the control group, and the formulations of ME00C1 and ME00C1A were administered respectively and simultaneously, the obese group was tube-fed with equal volume sterile water for eight weeks to evaluate the difference of body weight gain and body fat of each group; meanwhile, the body weight and the average food intake were recorded weekly. The rats were sacrificed, and epididymal fat, perinephric fat, and mesenteric fat were weighed and calculated to obtain visceral fat mass. All data are presented as Mean±SD. The letters a, b, c, and d represent the results of the statistics, the different letters represent statistical difference among the groups (p<0.05), and the identical letter represents no statistical difference among the groups (p>0.05).

Figure 5A:
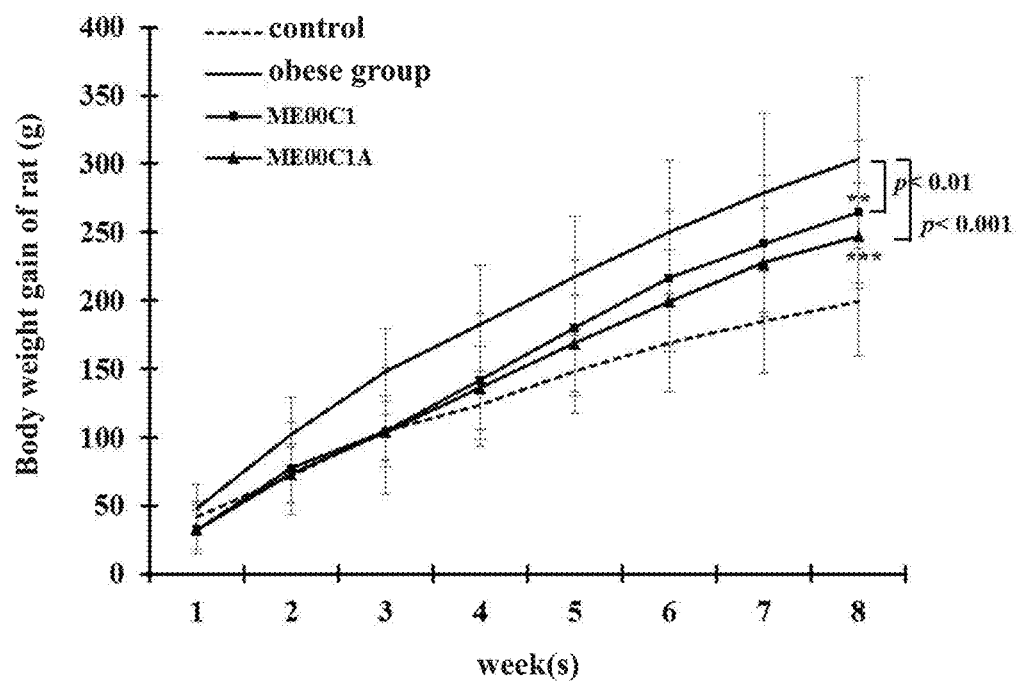
FIG. 5A illustrates the difference of body weight gain of rat administered with obesity induction and indicated composition simultaneously.
Figure 5B:
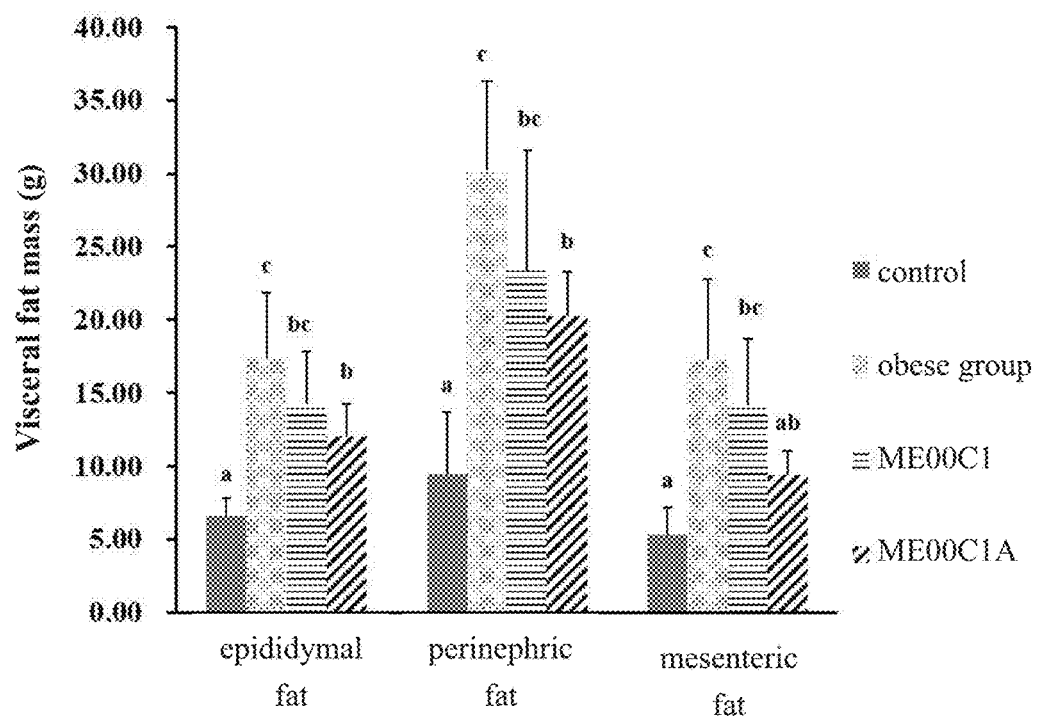
FIG. 5B illustrates the bar chart of fat mass of visceral fat of rat administered with high fat diet and indicated composition simultaneously.

As shown in FIG. 5A, the gains of body weight of the groups of the formulations ME00C1 and ME00C1A of the present invention were decreased significantly compared to that of obese group. The gain of body weight of the formulation ME00C1 was decreased by 23.0% (p<0.01 valued by t-test), and the gain of body weight of the formulation ME00C1A was decreased by 29.8% (p<0.01 valued by t-test). As shown in FIG. 5B, the visceral fat (comprising epididymal fat, perinephric fat, and mesenteric fat) of the formulation ME00C1A of the present invention was reduced significantly (p <0.05), wherein the visceral fat was decreased by 35.7%, representing that the formulation ME00C1A had the best reduction effect on the gain of body weight and body fat.

Even though numerous characteristics and advantages of the present invention are revealed and described as above, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for reducing body weight or body fat in a subject in need thereof, comprising administering to said subject an effective amount of a composition comprising a green tea extract and a turmeric extract, wherein the amount of the green tea extract: the turmeric extract is 30 wt%-70 wt%: 55 wt% to 20 wt%, respectively, and wherein the body fat is subcutaneous fat or visceral fat.

2. A method for treating overweight or obesity in a subject in need thereof, comprising administering to said subject a therapeutically effective amount of a pharmaceutical composition comprising a green tea extract and a turmeric extract, and further comprising a pharmaceutically acceptable carrier, wherein the amount of the green tea extract: the turmeric extract is 30 wt%-70 wt%: 55 wt% to 20 wt%, respectively.

3. The method of claim 2, wherein the formulation of the pharmaceutical composition is orally administered or administered by injection.

4. The method of claim 3, wherein the therapeutically effective amount of the pharmaceutical composition for a human is from 1.8 mg/kg to 145 mg/kg.

5. The method of claim 4, wherein the therapeutically effective amount of the pharmaceutical composition for a human is from 5.4 mg/kg to 70 mg/kg.

6. The method of claim 1, wherein the composition further comprises resveratrol in an amount between 0% and 30% based upon the total weight of the composition.

7. The method of in claim 1, the composition further comprises a pharmaceutically acceptable excipient.

8. The method of claim 1, the subject is a human or an animal.

9. The method of claim 1, the composition is orally administered or administered by injection.

10. The method of claim 9, wherein the therapeutically effective amount of the composition for a human is from 1.8 mg/kg to 145 mg/kg.

11. The method of claim 9, wherein the therapeutically effective amount of the composition for a human is from 5.4mg/kg to 70 mg/kg.

12. The method of claim 2, wherein the composition further comprises resveratrol in an amount between 0% and 30% based upon the total weight of the composition.

13. The method of claim 2, the overweight or obese subject is a human or an animal.

* * * * *